United States Patent [19]

Brown et al.

[11] Patent Number: 4,544,789

[45] Date of Patent: Oct. 1, 1985

[54] STEREOSELECTIVE SYNTHESIS OF INTERNAL OLEFINS

[75] Inventors: Theodore L. Brown, Urbana, Ill.; Philip O. Nubel, Westwood, N.J.

[73] Assignee: University of Illinois Board of Trustees, Urbana, Ill.

[21] Appl. No.: 529,891

[22] Filed: Sep. 6, 1983

[51] Int. Cl.$^4$ .............................................. C07C 2/34
[52] U.S. Cl. .................................. 585/511; 585/520; 502/152; 502/161; 204/162 R
[58] Field of Search ............... 585/511, 520; 502/152, 502/161; 204/162 R

[56] References Cited

U.S. PATENT DOCUMENTS

| | | | |
|---|---|---|---|
| 3,468,866 | 9/1969 | Alferor et al. | 502/152 |
| 3,725,305 | 4/1973 | Wilkinson | 502/161 |
| 3,917,730 | 11/1975 | Tkatchenko | 585/511 |
| 4,024,169 | 5/1977 | Pez | 585/511 |
| 4,210,524 | 7/1980 | Antos | 585/419 |
| 4,272,406 | 6/1981 | Beach et al. | 585/511 |
| 4,288,648 | 9/1981 | Beach et al. | 585/511 |
| 4,293,726 | 10/1981 | Beach et al. | 585/511 |

*Primary Examiner*—D. E. Gantz
*Assistant Examiner*—Cynthia A. Prezlock
*Attorney, Agent, or Firm*—Philip Hill

[57] ABSTRACT

Regioselective and stereoselective synthesis of trans-internal olefins is effected with transition metal catalyst complexes having pairs of associated active sites. Photolytic conditions are generally employed.

13 Claims, 2 Drawing Figures

STEREOSELECTIVE SYNTHESIS OF INTERNAL OLEFINS

This invention was made in the course of research sponsored by the National Science Foundation under Research Grant NSF CHE 81-19525.

BACKGROUND OF THE INVENTION

Catalytic synthesis of internal olefins has been effected by several methods. Cracking of aliphatic hydrocarbons generally yields a mixture of olefinic types. Oligomerization of light olefins, such as ethylene or propylene typically leads to a mixture, including branched chains particularly when employing olefins higher than ethylene. Neither method yields regio- or stereo-selective products. Isomerization of 1-alkenes (e.g., to 2-alkenes) has been made regioselective but typically yields mixtures of cis and trans stereoisomers. Reduction of acetylenes generally leads to cis internal olefins.

There is a need for specifically oriented olefins, particularly trans-internal olefins, in selective syntheses as, for example, in the preparation of biologically active agents. Filling such a need will almost certainly require highly specific catalytic agents.

SUMMARY OF THE INVENTION

This invention relates to the regioselective and stereoselective synthesis of trans-internal olefins, employing mild reaction conditions to prepare low molecular weight products from simple 1-olefins, such as ethylene and propylene.

This invention also relates to the development of novel catalyst compositions, comprising transition metal complexes having two associated reactive sites involving paired transition metal atoms.

This invention further relates to the photolytic promotion of catalyst formation and reactivity in the course of synthesis of trans-internal aliphatic olefins.

The process and catalyst of this invention permit the conversion, generally, of a 1-olefin having n carbon atoms principally to a trans-internal olefin having 2n carbon atoms, while limiting the remaining carbon-carbon double bond to the n-1 position. In a specialized instance, ethylene is converted to 1-butene and trans-3-hexene.

DESCRIPTION OF THE INVENTION

The process of this invention leads to the production of certain desirable internal olefins from two molecules of a relatively simple 1-olefin. The process may be generalized as the conversion of a 1-olefin, having n carbon atoms, into an internal olefin having 2n carbon atoms. The process is regioselective in that the surviving carbon-carbon double bond is located at the n-1 position. The process is stereoselective in that the olefinic configuration is predominantly of the trans orientation. For example, propylene is readily converted into trans-2-hexene. Interestingly, ethylene is first converted to 1-butene and then to trans-3-hexene.

Figure 1:
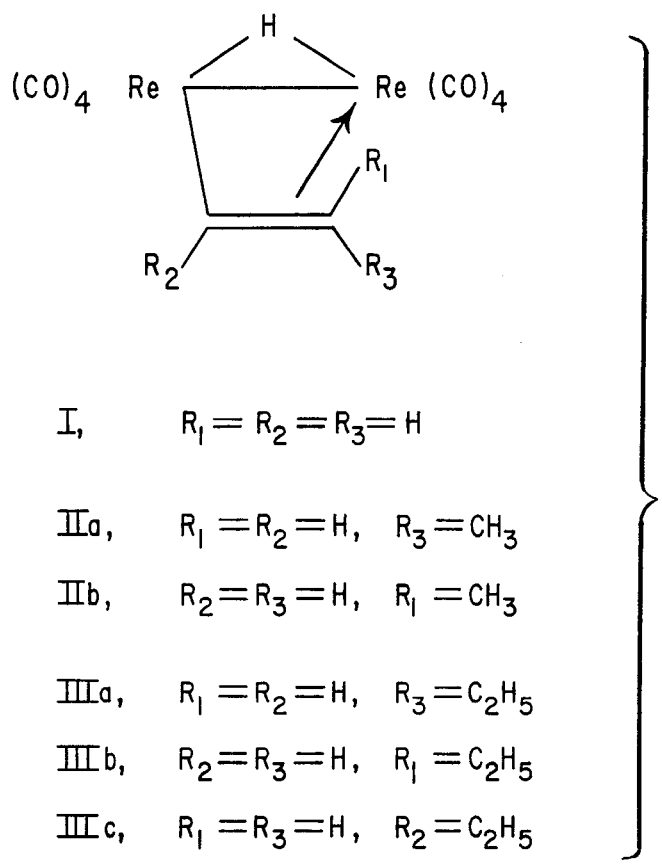
FIG. 1 presents a depiction of the structure of the precursor of one species of catalyst, illustrting the effective use of paired catalytic centers for stereoselective syntheses.

The process of this invention requires a catalyst having two related active catalytic sites. Without being limited thereby, it has been considered that paired, adjacent transition metal atoms may react in an orienting manner with an olefin, forming a sigma bond between one carbon and one transition metal atom while forming a coordinate pi bond with the second transition metal atom. This is shown schematically in FIG. 1 as the catalyst precursor postulated to be formed by reaction of a 1-olefin with dirhenium decacarbonyl. Two carbonyl ligands have been displaced and a hydrido bridge has been formed between the rhenium atoms which also serve to fix the olefinic moiety spatially. Precursors I, II, and III result, respectively, from reaction with ethylene, propylene, and butylene. In the latter two instances, IIa and IIIa are the thermodynamically most stable isomers of II and III, respectively.

Figure 2:
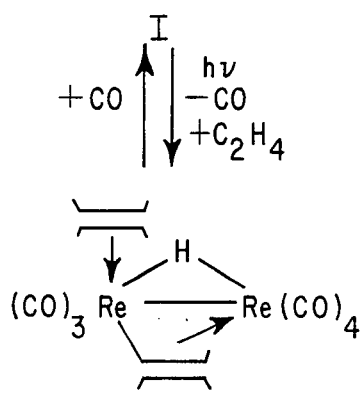
FIG. 2 presents a depiction of the structure of the catalyst, formed from the catalyst precursor of FIG. 1.

Addition of a 1-olefin to the precursor configuration, by insertion on the transition metal atom carrying the sigma bond after loss of an additional CO ligand, leads to the active catalyst complex. This is shown in FIG. 2. Subsequent dimerization of the carbon skeleton followed by thermal displacement, mechanistically leads to production of a single trans-internal olefin and restoration of the catalytic structure, by addition of 1-olefin, for use in a repeating reaction cycle.

The terminal olefin of this invention may be any 1-olefin, preferably an aliphatic 1-olefin. Reactivity is greatest with the olefins of lower molecular weight so that the preferred reactants are ethylene, propylene, butylene, pentene and hexene. Mixtures of olefins may also be employed, as, for example, ethylene and propylene.

The catalyst of this invention comprises a transition metal, such as rhenium, in a complex, generally comprising a requisite number of ligands such as carbonyl or phosphorus-donor groupings. A preferred catalyst composition comprises rhenium, preferably as a dirhenium carbonyl complex, derived from dirhenium decacarbonyl by reaction with a selected 1-olefin. Complex formation is preferably promoted with a photolytic source of ultra-violet radiation. A preferred photolysis source provides radiation at a wave length approximating 366 nanometers.

The various embodiments of this invention are generally conducted in the liquid phase in a solvent system. Preferred solvents, for both the catalyst complex and the olefin, include hexane, benzene and toluene, although any inert hydrocarbon that is normally liquid may be employed. The solvent should be especially free of moisture to avoid undesirable reactions of the catalyst complex which lead to loss of activity.

Catalyst formation and olefin synthesis both proceed readily under relatively mild reaction conditions. Generally, temperatures within the range from about 0° to about 100° C., preferably from about 20° to about 60° C., may be employed. Similarly, pressures within the range from about 0 to about 50 p.s.i.g., preferably from about 0 to about 10 p.s.i.g., may be employed.

The following examples are illustrative, without limitation, of the process and catalyst of this invention.

Dirheniumdecacarbonyl was purchased from Pressure Chemical Company and used without further purification. Hexane and toluene were treated with conc. $H_2SO_4$, rinsed with aqueous $NaHCO_3$, dried over $MgSO_4$, and fractionally distilled with $CaH_2$ under argon. CP grade ethylene, propylene, and 1-butene were obtained from Linde and used directly.

All photochemical reactions employed a General Electric 275 W Sunlamp and pyrex reaction vessels. The pyrex-filtered radiation consisted primarily of 366 nm wavelength; significant emission was also observed at 313, 334, 406, and 436 nm. Essentially no emission occurred below 297 nm.

EXAMPLE A

Compound IIa (see FIG. 1) was prepared by the photochemical reaction of $Re_2(CO)_{10}$ with propylene. $Re_2(CO)_{10}$ (0.300 g, 0.460 nmol) was dissolved in 10 ml. toluene under argon in a 50 ml. pyrex Schlenk flask. The solution was saturated with propylene (1 atm) and then photolyzed for 15–20 hours at 25°. (Sunlamp placed 5 cm from reaction vessel; solution maintained at room temperature by forced-air cooling.) IR analysis after photolysis indicated near complete (ca. 90%) conversion of $Re_2(CO)_{10}$ to IIa. Reaction of the remaining $Re_2(CO)_{10}$ was effected by vacuum degassing the reaction solution to remove evolved CO, resaturating with 1 atm propylene, and photolyzing 2–3 hours. IIa, a pale yellow oil, was isolated by column chromatography (4:1 hexane/$CH_2Cl_2$) and subsequent sublimation (0.1 nm, 60° C.).

EXAMPLE B

Compound IIIa (see FIG. 1) was prepared by the method of Example A, employing 1-butene instead of propylene Compound IIIa was also a pale yellow oil at 25° C.

EXAMPLE C

Compound I (see FIG. 1) was prepared by thermal reaction of IIa with ethylene. Compound IIa (0.23 g, 0.36 mmol) was dissolved in 10 ml. toluene under 1 atm $C_2H_4$ and stirred for 10 hours at 40° C. The solution was then vacuum-degassed (at 25°), resaturated with 1 atm. $C_2H_4$, and stirred at 40° for an additional 10 hours. The degas/ethylene-treatment procedure was repeated, after which conversion of IIa to I was complete. Compound I, a pale yellow crystalline solid, was purified by column chromatography (4:1 hexane/$CH_2Cl_2$) and subsequent sublimation (0.1 mm, 70° C.).

EXAMPLE D

Photolysis of a toluene or hexane solution of I at 25° resulted in little or no reaction other than slow decomposition to $[Re(CO)_3OH]_4$, presumably due to the presence of trace water in solution.

EXAMPLE E

Photolysis of a toluene solution of IIa at 25° resulted in rapid isomerization to IIb. Within 30 minutes, a stationary state mixture of the two isomers was achieved in which the ratio of IIa to IIb was 1.4:1. Due to the tendency of IIb to isomerize thermally to IIa, this measurement was performed by immediately chilling the solution after photolysis and recording the NMR at low temperature (−20° C.). Photolysis at 5° C. gave a stationary state IIa/IIb mixture of the same composition. However, photolysis at 45° C. resulted in a IIa:IIb=5.5:1 steady-state mixture.

EXAMPLE F

Photolysis of a toluene solution of IIIa at 25° afforded a 1.7:1 IIIa/IIIb stationary state composition within 30 min.

EXAMPLE G

Photolysis of a toluene solution of I at 25° in the presence of 1 atm ethylene resulted in production of compounds IIIa-c. No reaction was observed in the absence of irradiation. After short photolysis periods (less than 15 min., corresponding to less than 15% reaction of I), isomer IIIc predominated; an approximate 9:2:1 ratio of IIIc:IIIa:IIIb was observed by NMR. Due to the tendency of IIIc and IIIb to isomerize thermally to IIIa, this measurement was performed by immediately chilling the solution after photolysis and recording the NMR at low temperature (−20°). Compound IIIc still predominated after longer photolysis times (1-5 h) although the amount relative to IIIa,b was smaller, probably due to thermal isomerization. No other organometallic products were detected except for $[Re(CO)_3OH]_4$. Slow production of this complex was observed, presumably due to the presence of trace water in solution.

Production of free butene and hexene occurred during the photolysis; the butene was more than 95% 1-butene, while the hexene was primarily (80–90%) trans-3-hexene. Formation of these olefins did not occur at 25° C. without irradiation. After 1.0 hour photolysis at 25°, 50–60% conversion of I to III was observed along with 0.03 equivalents 1-butene. (One equivalent represents the initial molar amount of I, here $2.47 \times 10^{-5}$ mol. in 2.0 ml. toluene). The rate of butene production increased to approximately 0.1 equiv/h within 1–2 hours; 0.12, 0.32, 0.51, and 2 equiv. 1-butene were observed after 2, 4, 6 and 24 hours photolysis, respectively. Hexene production was somewhat slower; 0.20 and 0.7 equiv. were detected after 6 and 24 hours photolysis, respectively. The isomeric distribution is 80–90% trans-3-hexene, ca. 10% cis-3-hexene, 3–6% 1-hexene, ca. 5% 2-hexene, and essentially no branched hexenes. Little or no production of octenes occurred (<0.01 equiv after 6 hours photolysis).

EXAMPLE H

Employing the procedure of Example G, photolysis of I in the presence of 1 atm ethylene (toluene solution) at 50° C. resulted in more rapid generation of butene and hexene. After 1 hour photolysis, 0.03 equiv. free 1-butene was observed. However, the rate of butene production increased to 0.3–0.4 equiv/h within 1–2 hours; 0.35, 1.2, and 1.9 equiv butene were detected after 2, 4, and 6 hours photolysis at 50°, respectively. The butene was predominantly (>90%) 1-butene, although the relative amount of 2-butene (primarily trans) accounted for 4% of the evolved butene after 4 hours photolysis, 8% after 6 hours photolysis. The hexene generated, 0.35 equiv after 6 hours photolysis, was mostly trans-3-hexene, with 10–15% 1-hexene and 5–10% 2-hexene. Decomposition of I to $[Re(CO)_3OH]_4$ occurs at the same rate as in photolyses at 25°.

EXAMPLE I

Addition of 1 atm. ethylene to a photostationary state mixture of IIa,b (1.4:1 a:b at 25°, toluene solution, see Example E) followed by continued photolysis at 25° resulted in slow production of free pentene, primarily trans-2-pentene. Less than 0.1 equiv pentene was evolved after 1 hour irradiation. Pentene formation did not occur thermally at 25°. The isomeric distribution, as measured after 15 and 60 min photolysis, was 85% trans-2-pentene, 10-12% cis-2-pentene, and 3-5% 1-pentene.

EXAMPLE J

Photolysis of a toluene solution of compound of IIa at 25° in the presence of 1 atm. propylene resulted in the slow production of hexene, predominantly 2-hexene. As in the absence of excess propylene, a 1.4:1 photostationary state mixture of IIa:b was reached within 30 min. irradiation time. After 1.0, 7.5, and 20 hours photolysis, gas chromatographic analysis indicated 0.015, 0.10, and 0.19 equiv hexene, respectively, present in the reaction solution. (As before, one equivalent represents the initial molar amount of II.) Production of hexene ceased when photolysis was discontinued. No $C_2$, $C_4$, or $C_5$ products were detected. The isomeric distribution of hexenes, which remained essentially constant from 1-20 hours photolysis, was 50% trans-2-hexene, 35% cis-2-hexene, 5% 1-hexene, 5% trans-4-methyl-2-pentene, and $\leq$5% 3-hexene plus other branched hexenes. After 20 hours irradiation, about half the initial quantity of compound II had decomposed to $[Re(CO)_3OH]_4$.

EXAMPLE K

When the procedure of Example J was performed at 45° C., the hexene distribution changed, although the rate of production remained about the same. After 0.5, 1.0, and 6.5 hours photolysis, analysis indicated 0.007, 0.014, and 0.06 equiv hexene, respectively, evolved. The isomeric distribution, as measured after 1 and 6.5 hours, was 75% trans-2-hexene, 10-15% cis-2-hexene, 2-3% 1-hexene, 7-9% trans-4-methyl-2-pentene, and <5% 3-hexene plus other branched hexenes. Again, no $C_2$, $C_4$, or $C_5$ products were observed. $C_9$ species (nonenes) were also not detected. As in the absence of excess propylene, a 5.5:1 stationary state mixture of IIa:b was reached within 30 min.

EXAMPLE L

After room temperature photolysis of a toluene solution of I for 45 minutes while bubbling ethylene through the solution, the IR spectrum was dominated by I and hydridobutenyl dirhenium octacarbonyl species. Other weaker bands disappeared when the solution was subsequently treated with CO. These weaker bands at 2105, 2044 and 1920 cm$^{-1}$ have been assigned to the active catalyst complex species.

When photolysis was discontinued, hexene (trans-3-hexene) was produced with continuing ethylene flush. After 40 hours thermal reaction at 25° C. under 1 atm. ethylene, 0.74 equiv hexene was observed in solution.

We claim:

1. A stereoselective process for the synthesis of internal olelfins from terminal olefins, said terminal olefins having a lower molecular weight, comprising the steps of:
   (a) affording a transition metal catalyst complex having two associated reactive sites, wherein the transition metal catalyst complex comprises the photolysis reaction product of a terminal olefin with two associated reactive sites of paired transition metal atoms;
   (b) contacting at least one terminal olefin with the catalyst complex; and
   (c) recovering the internal olefin product therefrom.
2. The process of claim 1 wherein the terminal olefin is an aliphatic olefin.
3. The process of claim 2 wherein the terminal olefin is selected from the class consisting of ethylene, propylene, 1-butylene, 1-pentene, 1-hexene and mixtures thereof.
4. The process of claim 1 wherein the transition metal complex comprises the photolysis reaction product of a terminal olefin with dirhenium decacarbonyl.
5. The process of claim 1 wherein the photolysis is effected with radiation having a wave length of about 366 nanometers.
6. The process of claim 1 wherein the internal olefin synthesis is effected at a temperature within the range from about 0° to about 100° C. and at a pressure within the range from about 0 to about 50 p.s.i.g.
7. The process of claim 6 wherein the reaction temperature is within the range from about 20° to about 60° C. and the pressure is within the range from about 0 to about 10p.s.i.g.
8. The process of claim 1 wherein the terminal olefin and the transition metal catalyst complex are dissolved in a common solvent therefor.
9. The process of claim 8 wherein the solvent is selected from the class consisting of hexane, benzene and toluene.
10. The process of claim 1 wherein a major portion of the internal olefin product is a trans-internal olefin product.
11. The process of claim 10 wherein the terminal olefin is ethylene and the internal olefin product is trans-3-hexene.
12. The process of claim 10 wherein the terminal olefin is propylene and the internal olefin product is trans-2-hexene.
13. A process for the production of trans-3-hexene from ethylene, as a dilute solution in toluene, in the presence of a catalyst complex, said complex resulting from the photolytic reaction of ethylene with dirhenium decacarbonyl, said process being conducted at a temperature within the range from about 20° to about 60° C. and at a pressure within the range from about 0 to about 10 p.s.i.g.

* * * * *